United States Patent [19]

Whitmore et al.

[11] Patent Number: 4,546,174

[45] Date of Patent: Oct. 8, 1985

[54] PROCESS FOR THE PREPARATION OF ALIPHATIC AZO COMPOUNDS USING AN AMINE COUPLING

[75] Inventors: Martyn W. Whitmore; Michael D. Pollard; Stephen R. Smythe, all of Cambridge, England

[73] Assignee: FBC Limited, Cambridge, England

[21] Appl. No.: 578,130

[22] Filed: Feb. 8, 1984

Related U.S. Application Data

[63] Continuation of Ser. No. 218,421, Dec. 19, 1980, abandoned.

[30] Foreign Application Priority Data

Dec. 20, 1979 [GB] United Kingdom ................ 7943862

[51] Int. Cl.$^4$ .......................................... C07C 107/02
[52] U.S. Cl. .................................. 534/838; 534/886; 548/356; 548/358
[58] Field of Search ................ 260/192; 548/356, 358; 534/838, 886

[56] References Cited

U.S. PATENT DOCUMENTS

| | | | |
|---|---|---|---|
| 2,711,405 | 6/1955 | Anderson | 260/192 |
| 2,713,526 | 6/1955 | DeBenneirlle | 260/192 |
| 3,346,554 | 10/1967 | Fuchs | 260/192 |
| 4,028,345 | 6/1977 | Moore, Jr. | 260/192 |
| 4,051,124 | 9/1977 | Moore, Jr. | 260/192 |
| 4,272,435 | 6/1981 | Matsuda et al. | 260/192 |

FOREIGN PATENT DOCUMENTS 1168406  10/1969  United Kingdom ................ 260/192

OTHER PUBLICATIONS

Miller et al., Sidgwick's "The Organic Chemistry of Nitrogen", Clarendon Press: Oxford (1966), pp. 127–128.

Primary Examiner—Charles F. Warren
Attorney, Agent, or Firm—Morgan, Finnegan, Pine, Foley & Lee

[57] ABSTRACT

There is described a process for the production of a compound of formula I,

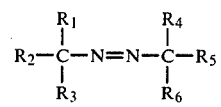

in which at least one each of $R_1$, $R_2$ and $R_3$, and of $R_4$, $R_5$ and $R_6$, represents an electron withdrawing group, or one of $R_1$, $R_2$ and $R_3$ together with one of $R_4$, $R_5$ and $R_6$ form a —CO— group, and the remainder of $R_1$, $R_2$, $R_3$, $R_4$, $R_5$ and $R_6$, which may be the same or different, each represent an electron withdrawing group, alkyl, cycloalkyl, phenyl or phenylalkyl, or $R_1$ and $R_2$, or $R_4$ and $R_5$, and $R_1$ and $R_4$, may together form a —$(CH_2)_n$—chain, in which n is a whole number up to 5,
the alkyl, cycloalkyl, phenyl or phenylalkyl group or the —$(CH_2)_n$—chain optionally being substituted, which comprises reacting a compound of formula II,

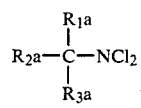

in which $R_{1a}$, $R_{2a}$ and $R_{3a}$ have the same significances as $R_1$, $R_2$, and $R_3$ above, and some additional significances,
with a compound of formula III,

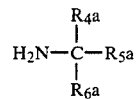

in which $R_{4a}$, $R_{5a}$ and $R_{6a}$ have the same significances as $R_4$, $R_5$ and $R_6$ above, and some additional significances,
the reaction being carried out in an aqueous medium in the presence of a base and a surfactant.

10 Claims, No Drawings

PROCESS FOR THE PREPARATION OF ALIPHATIC AZO COMPOUNDS USING AN AMINE COUPLING

This is a continuation, of application Ser. No. 218,421 filed Dec. 19, 1980 abandoned.

This invention relates to an improved process for the preparation of aliphatic azo compounds.

The symmetrical and unsymmetrical azobis(alkanenitriles) and their analogues, either as single compounds or as mixtures of one or more azo compounds, have been recognised for many years as useful foaming agents and free-radical polymerisation initiators.

These compounds are made commercially from hydrazine and a cyanohdyrin, but the cost of producing hydrazine of sufficient purity has made this process unattractive. The compounds have also been made by the interaction of the appropriate alpha cyano amines with aqueous hypochlorite solutions, e.g. as described in U.S. Pat. Nos. 2,713,576 and 4,051,124. However aqueous hypochlorite solutions are expensive to produce and are bulky to transport and handle thus requiring a relatively large plant. Furthermore the heat generated in the hypochlorite process is difficult to remove at the low reaction temperature and can have deleterious effects on the reaction. It is also known, for example from U.S. Pat. No. 3,346,554, to react chlorine with certain amino compounds to produce the corresponding dichloramines and then to couple the dichloramines in the presence of a base to produce the corresponding symmetrical azo compounds. However an essential feature of this process is that it be carried out in an organic solvent. A modification of this process has been suggested in which up to 0.5 of a mole of the corresponding amino compound is added, together with the base, for each mole of dichloroamine compound. Essentially this known process involves the coupling of 2 moles of the dichloramine. Thus for example:

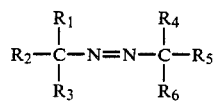

This process however uses large quantities of both chlorine and base and therefore produces large quantities of salt. Also, for reasons of economy, it requires the recovery of the organic solvent.

We have now surprisingly found that a dichloramine can be coupled with an amine in water, which is a poor solvent for the dichloramine, to produce the desired azo compound.

Thus according to our invention we provide a process for the production of a compound of formula I,

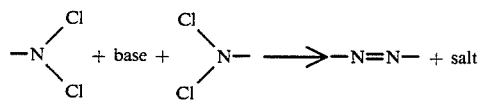

in which at least one of $R_1$, $R_2$ and $R_3$, and at least one of $R_4$, $R_5$ and $R_6$, represents an electron withdrawing group, or one of $R_1$, $R_2$ and $R_3$ together with one of $R_4$, $R_5$ and $R_6$ form a —CO— group, and the remainder of $R_1$, $R_2$, $R_3$, $R_4$, $R_5$ and $R_6$, which may be the same or different, each represent an electron withdrawing group, alkyl, cycloalkyl, phenyl or phenylalkyl, or $R_1$ and $R_2$, $R_4$ and $R_5$, and $R_1$ and $R_4$, may together form a —$(CH_2)_n$—chain, in which n is a whole number up to 5, the alkyl, cycloalkyl, phenyl or phenylakyl group or the —$(CH_2)_n$ chain optionally being substituted by one or more hydroxy groups or acyl derivatives thereof, alkoxy groups, halogen atoms, or carboxylic acid groups or salts or esters thereof, which comprises reacting one or more compounds of formula II,

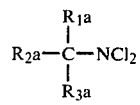

in which $R_{1a}$, $R_{2a}$ and $R_{3a}$ have the same signficances as $R_1$, $R_2$, and $R_3$ above, and additionally $R_{1a}$ may represent a group —$(CH_2)_n$—$CR_5R_6$—$NCl_2$ in which n, $R_5$ and $R_6$ are as defined above, or $R_{3a}$ may represent a group —$COCR_5R_6NCl_2$ in which $R_5$ and $R_6$ are as defined above, with one or more compounds of formula III,

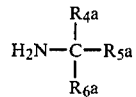

in which $R_{4a}$, $R_{5a}$ and $R_{6a}$ have the same significances as $R_4$, $R_5$ and $R_6$ above, and additionally $R_{4a}$ may represent a group —$(CH_2)_n$—$CR_2R_{13}$—$NH_2$ in which n, $R_2$ and $R_3$ are as defined above, or $R_{6a}$ may represent a group —$COCR_2R_3$—$NH_2$ in which $R_2$ and $R_3$ are as defined above, or causing an intramolecular reaction in a compound of formula V,

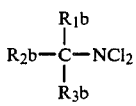

in which $R_{1b}$, $R_{2b}$ and $R_{3b}$ have the same significances as $R_1$, $R_2$ and $R_3$ above and additionally $R_{1b}$ may represent a group —$(CH_2)_n$—$CR_5R_6$—$NH_2$ in which n, $R_5$ and $R_6$ are as defined above or $R_{3b}$ may represent a group —$CO$—$CR_5R_6$—$NH_2$ in which $R_5$ and $R_6$ are as defined above, the reaction being carried out in an aqueous medium in the presence of a base and a surfactant.

An excess of the compound of formula III may be used if desired, but we prefer to use an equimolar proportion or slightly less than an equimolar proportion of the compound of formula III with respect to the compound of formula II, e.g. from 0.6 to 1.0 moles, and preferably from 0.85 to 1.0 moles, of the compound of formula III for each mole of the compound of formula II.

The reaction is preferably carried out in the substantial absense of any solvent other than water as the presence of other solvents tends to have a deleterious effect on the reaction, e.g. to reduce the yield.

The base may be an alkali or alkaline earth metal hydroxide or a mixture thereof. We prefer to use an alkali metal hydroxide, e.g. sodium hydroxide.

We prefer to use at least sufficient base to neutralise any HCl generated during the coupling, and more particularly we prefer to use an excess of base to provide a high pH (e.g. greater than 11, and preferably greater than 12) at the end of the reaction. We thus prefer to use from 2.0 to 2.5, preferably from 2.2 to 2.5 moles of base for each mole of the compound of formula II. We also prefer to use an initial concentration of from 2 to 20% w/w of the dichloramine of formula II in the reaction medium.

The reaction may conveniently be carried out at a temperature above which the reaction medium is liquid and below which there is no substantial decomposition of the azo compound, e.g. a temperature of from about $-5°$ to $+50°$ C., preferably at from $15°$ to $35°$ C., and especially $20°$ to $30°$ C. The reaction is exothermic and cooling will, in general, be desirable. However, the heat produced per unit of product is less than with the prior art hypochlorite reaction, thus facilitating control of the reaction.

The compounds of formulae II and III may be derived from the same amine, thus yielding a symmetrical compound of formula I, or from different amines yielding a mixture of symmetrical and unsymmetrical compounds of formula I. The proportions of the compounds in a mixed product may be altered by controlling the rate of mixing of the compounds of formulae II and III.

Mixtures of compounds of formula I may be used as such or may be separated into their components using a conventional processes known per se, e.g. fractional crystallisation.

The reaction is carried out in the presence of a surfactant or a mixture of surfactants. Surfactants with HLB numbers within the range of 8.0 to 35.0, are preferred. We also prefer cationic surfactants.

The amount of surfactant may vary widely. As little as 0.25% by weight of surfactant based on the compound of formula II can be used and while the upper limit is not critical, there is no advantage in using more than 10% by weight. The preferred range is 1.0 to 4.0%, and more preferably 1.0 to 2.0% by weight of surfactant based on the compound of formula II.

Suitable cationic surfactants include phosphonium salts and various types of nitrogen containing compounds such as fatty alkyl amines and their salts and quaternary ammonium compounds, and more specifically tetraalkyl ammonium compounds. Tetraalkyl ammonium halides, for example tetraalkyl ammonium chlorides or bromides are preferred, e.g. alkytrimethylammonium chlorides or bromides. The tetraalkyl ammonium bromides are considered the most preferred surfactants. We also prefer the reaction to be carried out in the presence of bromide ion, e.g. from 0.2 to 1.0 moles of bromide ion per mole of surfactant. The presence of bromide ion tends to accelerate the reaction and to give an enhanced yield and quality of product.

Representative examples of suitable tetraalkyl ammonium surfactants are:

| Compound | Trade Name |
| --- | --- |
| Disoya dimethyl ammonium chloride | 'Arquad' (registered Trade Mark) 25-75 |
| Ditallow imidazolinium quaternary salt | 'Alkaquat' T |
| Cetyl trimethyl ammonium bromide | 'Retarder' LAN |
| Quaternised polyoxyethylene cocoamine | 'Ethoquad' (registered Trade Mark) C/25 |
| Tallow Trimethyl ammonium chloride | 'Arquad' T-50 |
| Tetradecyl trimethyl ammonium chloride | |
| Dodecyl trimethyl ammonium chloride | 'Arquad' 12-50 |
| Cetyl trimethyl ammonium chloride | 'Arquad' 16-29 |
| Octadecyl trimethyl ammonium chloride | 'Arquad' 18-50 |

We prefer those surfactants which are formulated in an aqueous medium.

The reaction may conveniently be carried out at atmospheric pressure. The surfactant is preferably mixed with the water, the base and the starting dichloramine, and the compound of formula II is then added gradually. Alternatively the base and the amine of formula III may be added concurrently to the remaining components of the reaction to maintain the desired pH. The course of the reaction may, if desired, be monitored and controlled by means of the redox potential of the reaction mixture, for example by carrying out the reaction to a redox end point of 370 to 430 mv, e.g. about 400 mv.

The process gives a product mixture which may be, unusually, partially or almost entirely an emulsion. Conventional techniques for breaking emulsions may, if desired or necessary, be employed to help in the isolation of the product.

In the case where the starting compound is 2-amino-2-methylproprionitrile, the product formed appears to be an emulsion of milk-like appearance, but the product is entirely a solids suspension and therefore an emulsion breaking step is not generally necessary.

The compounds of formula II and V are preferably made by reaction of one or more compounds of formula III with elemental chlorine.

The reaction preferably takes place in water. We prefer to use a concentration of from about 2 to 20% w/w of the compound(s) of formula III in water.

The chlorine may be passed into the solution of the compound of formula III until no further chlorine is absorbed or until a redox end-point (at 1030 to 1100 preferably 1030 to 1060 mv) is reached.

The chlorination reaction produces by product HCl which may, if desired, be removed before further reaction of the product with the amine of formula III, for example by conventional techniques such as separation of an aqueous HCl containing phase from an oily dichloramine phase, e.g. by decantation. Alternatively the by product HCl may be neutralised continuously during the chlorination by addition of a suitable base, e.g. an alkali or alkaline earth metal hydroxide, carbonate or bicarbonate. If the HCl is not removed before reaction with the amine of formula III more base will be required to neutralise the pre-existing HCl in the reaction of the dichloramine with the compound of formula III.

The chlorination reaction is exothermic and in general cooling is necessary to maintain the temperature in range $0°$ to $40°$ C. and preferably in the range $15°$ to $35°$ C.

The chlorination reaction may be carried out on a batch or on a continuous basis.

According to a further feature of our invention we provide a process for the production of a compound of formula I which comprises reacting a compound of formula III with elemental chlorine and reacting the resulting dichloramine with a compound of formula III in an aqueous medium and in the presence of a base and preferably also a surfactant.

When $R_1$, $R_2$, $R_3$, $R_4$, $R_5$ or $R_6$ is an electron withdrawing group it may be, for example, a group —COR, —COOR, —COOM or —CN, wherein R represents alkyl, cycloalkyl, aryl (e.g. phenyl) or aralkyl (e.g. benzyl), and M represents hydrogen or a cation. We prefer $R_1$, $R_2$, $R_4$ and $R_5$ to be selected from alkyl, cycloalkyl, phenyl or phenylalkyl, or $R_1$ and $R_2$, or $R_4$ and $R_5$; $R_1$ and $R_2$ and $R_4$ and $R_5$; or $R_1$ and $R_4$ together to form a —$(CH_2)_n$—chain; and $R_3$ and $R_6$ to represent an electron withdrawing group, or $R_3$ and $R_6$ together to form a —CO— group. We also prefer that $R_3$ and $R_6$ do not form a —CO— group when $R_1$ and $R_4$ together form a —$(CH_2)_n$—chain. When $R_1$ to $R_6$ optionally substituted groups we prefer them to carry only one substituent, e.g. an —OH or a C 2 to 6 alkanoyl derivative thereof, a chlorine, bromine, iodine or fluorine atom, a carboxylic acid group or salt thereof, or a C 1 to 6 alkyl ester thereof. We prefer $R_3$ and $R_6$ to both be —CN.

We prefer each of $R_1$ to $R_6$ to contain up to and including 10, and more preferably up to and including 6, carbon atoms. Thus $R_1$, $R_2$, $R_4$ and $R_5$ may each be alkyl C 1 to 6, e.g. methyl, 2-methylpropyl, 3-methylbutyl or methoxybutyl or $R_1$ and $R_2$ and/or $R_4$ and $R_5$ may together form a cyclohexyl or cyclopentyl ring. We prefer n to be 4 or 5 in $R_1+R_2$ or $R_4+R_5$ and to be 1 or 2 in $R_1+R_4$. In particular we prefer $R_1$, $R_2$, $R_4$ and $R_5$ each to be methyl and $R_3$ and $R_6$ each to be —CN. When M is a cation it may be, for example, a sodium or potassium ion.

The compounds of formula III are either known or may be made from known compounds using conventional techniques known per se.

As indicated above the compounds of formula I (including mixtures thereof) are useful as free-radical polymerisation initiatiors and as foaming agents.

The compound of Example 8 is a new compound and is particularly advantageous for the above uses.

The invention is illustrated, but in no way limited, by the following Examples.

EXAMPLE 1

2,2'-Azobis(2-methyl-propanenitrile)

Chlorine gas is bubbled into a stirred vessel containing 350 mls of water and 30 gms of 2-amino-2-methyl-propanenitrile (of 79% purity the balance comprising mainly water) maintained at 20° C. by slight external cooling. The chlorine flow is stopped when the redox potential reaches 1030 to 1050 mv and chlorine gas is observed over the liquid. Two equivalents of chlorine are required.

The resulting aqueous dispersion of N,N-dichloro-2-amino-2-methyl-propanenitrile is adjusted to pH 7 with caustic soda, maintaining the temperature at 20° C. by slight cooling, and 3 ml of 'Arquad 16–29%' (a commodity surfactant comprising an aqueous solution of mainly cetyl trimethyl ammonium chloride) is added. A further 2.2 equivalents of caustic soda are added and 26 gm of 2-amino-2-methyl-propanenitrile is added over 20 minutes with cooling to maintain a temperature of 20° C.

The resulting aqueous slurry is filtered, washed and dried to yield 42.2 gm of the title compound (98% yield).

EXAMPLE 2

2,2'-Azobis(2-methyl-propanenitrile)

30 gm of 2-amino-2-methyl-propanenitrile (of 80% purity) is added intermittently to a stirred vessel containing 350 mls of water held at 20° C. and into which a constant stream of chlorine gas is passed, such that the redox potential in the vessel is held at 1050 mv.

The resulting aqueous dispersion of N,N-dichloro-2-amino-2-methyl-propanenitrile is then treated by the method of Example 1 to yield the title compound in 98% yield.

EXAMPLE 3

2,2'-Azobis(2-methyl-propanenitrile)

30 g of 2-amino-2-methyl-propanenitrile (of 79% purity) is converted to N,N-dichloro-2-amino-2-methyl-propanenitrile by the method of Example 1. The aqueous dispersion of N,N-dichloro-2-amino-2-methyl-propanenitrile is allowed to settle and the upper acidic aqueous layer is replaced by an equal volume of water.

3 ml of 'Arquad 16-29' is added, followed by 2.2 equivalents of caustic soda. While maintaining the temperature at 20° C., 26 mg of 2-amino-2-methyl-propanenitrile is added over 20 minutes and the title compound is isolated as in Example 1. Yield 96%.

EXAMPLE 4

1,1'-Azobis(1-cyanocyclohexane)

23 g of 1-amino-1-cycanocyclohexane (91% assay made by the method of U.S. Pat. No. 3,131,210) is dichlorinated by the method of Example 2 at 20° C. to a redox potential of 1100 mv.

The pH is adjusted to 7 at 20° C. and 3 ml of 'Arquad 16–29' is added followed by a further 2.2 equivalents of caustic soda and 23 g of 1-amino-1-cyanocyclohexane over 20 minutes with cooling to maintain a temperature of 20° C. The reaction is stirred for a further five minutes and filtered, washed and dried to yield 36.7 g of the title compound, as a white solid (89%).

EXAMPLE 5

2,2'-Azobis(2,4-dimethylpentanentrile)

In a similar manner to Example 4 16 g of 2-amino-2,4-dimethylpentanenitrile is chlorinated and then coupled with a further 16 g of 2-amino-2,4-dimethylpentanenitrile to yield, after filtration and drying 19 gm of 2,2'-azobis (2,4-dimethylpentanetrile) 65%.

EXAMPLE 6

2,2'-Azobis(2-methylpropanenitrile)

2,2'-Azobis(2,4-dimethylpentanentrile)

2-[(1-Cyano-1-methylethyl)azo]-2,4-dimethylpentanentrile 30 of 2-amino-2-methylpropanenitrile (79%) is dichlorinated by the method of Example 2. The pH is then adjusted to 7 to 20° C., 3 ml of 'Arquad 16–29' is added followed by a further 2.2 equivalents of caustic soda. To this is then added, with cooling to maintain a temperature of 20° C., 38 gm of 2-amino-2,4-dimethyl-pentanentrile (93%) over 20 minutes.

After a further the minutes at 20° C. the solid is removed by filtration (28 gm) and the liquors are extracted with methylene chloride to yield 17 gm of semi-solid oil.

The yield of combined azo compounds is 86% and the products are 2,2'-azobis(2-methylpropanenitrile), 2,2'-dimethylpentanetrile) and 2-[(1-cyano-1-methylethyl)azo-]-2,4-dimethylpentanenitrile in a ratio of approximately 3.5 to 1 to 4.0.

EXAMPLE 7

2,2'-Azobis(2-methylpropanenitrile)

2-[(1-Cyano-1-methylethyl)azo]-1,2-dimethylpentanenitrile 2,2'-Azobis(2,4-dimethylpentanenitrile)

In the manner of Example 6, but by first chlorinating 2-amino-2,4-dimethylpentanenitrile and then coupling with 2-amino-2-methyl-propanenitrile in the presence of caustic soda and surfactant (in the same proportions as in Example 6), over one hour, a 42% yield of mixed azo compounds was obtained comprising approximately 1 part 2,2'-azobis(2-methylpropanenitrile), 10 parts 2-[(1-cyano-1-methylethyl)azo]-1,2-dimethylpentanitrile and 40 parts 2,2'-azobis(2,4-dimethylpentanenitrile).

EXAMPLE 8

2,2'-Azobis(2,5-dimethylhexanenitrile)

30 g of 94% pure 2-amino-2,5-dimethylhexanenitrile is chlorinated in water at 1080 mv by the method of Example 2. To the resulting aqueous dispersion of 2-dichloroamino-2,5-dimethylhexanenitrile, following the method of Example 1, caustic soda, wetter, and a further 20 g of 2-amino-2,5-dimethylhexanenitrile are added and the suspension is filtered to yield 40.6 g of the title compound as a creamy white solid, mp 56°–58° C. (88%).

EXAMPLE 9

3,3,5,5-Tetramethylpyrazol-4-one 3,5 g of 2,4-diamino-2,4-dimethylpentan-3-one (of 58% purity) is chlorinated by the method of Example 1 in water until four equivalents of chlorine have been absorbed. The resulting aqueous dispersion of 2,4-bis(dichloroamino)-2,4-dimethyl-pentan-3-one is adjusted to pH 7 with caustic soda, and 0.25 ml of 'Arquad 16-29', and a further 2.2 equivalents of caustic soda are added with cooling to maintain a temperature of 20° C.

A further 2.2 g of 2,4-diamino-2,4-dimethylpentan-3-one, in water, (50 ml) is then added slowly over 40 minutes at 20° C. The resulting aqueous solution is then extracted with dichloromethane and the evaporated extract yields 2.2 g of pale yellow solid identified as pure title compound, by thin layer chromatographic comparison with an authentic sample (yield 71%).

EXAMPLE 10

3,3,5,5-Tetramethylpyrazol-4-one 3.6 g of 2,4-diamino-2,4-dimethylpentan-3-one (of 73% purity) is added to 250 mls of water and chlorinated by the method of Example 1 until two equivalents of chlorine have been absorbed.

The solution is carefully adjusted to pH 7, 0.25 ml of Arquad 16-29 is added, and a further two equivalents of caustic soda are added dropwise with cooling to maintain a temperature of 20° C.

The resulting solution is extracted and evaporated as in Example 9 to yield 1.98 g of the title compound as a pale brown semi solid product.

EXAMPLE 11-21

2,2'Azobis(2-methylpropanenitrile)

In the manner of Example 2, 2-amino-2-methylpropanenitrile was chlorinated in water and coupled with further 2-amino-2-methylpropanenitrile in the presence of caustic soda and 'Arquad 16-29', with coupling temperatures, feed rates of 2-amino-2-methylpropanenitrile to the coupling stage and yields as indicated below.

| Temp (°C.) | Feed Rate (gm/min) | Yield (%) |
|---|---|---|
| 10 | 1.2 | 79.7 |
| 10 | 3.0 | 67.0 |
| 10 | 4.0 | 59.0 |
| 20 | 0.8 | 91.8 |
| 20 | 2.0 | 88.0 |
| 20 | 3.2 | 88.0 |
| 20 | 3.8 | 86.0 |
| 30 | 1.0 | 95.8 |
| 30 | 2.0 | 86.4 |
| 30 | 3.8 | 86.7 |
| 40 | 3.0 | 69.3 |

EXAMPLES 22-29

2,2'-Azobis(2-methylpropanenitrile)

Using the method and quantities of Example 2, but replacing the 'Arquad 16-29' by the surfactants listed below (in the proportions of 1.6% wt/wt based on total 2-amino-2-methylpropanenitrile used) gave 2,2'-azobis(2-methylpropanenitrile) in the yields indicated.

| | Surfactant | Yield (%) |
|---|---|---|
| CATIONIC | Tetra-n-butylammonium bisulphate | 79.9 |
| | Tri-caprylmethylammonium chloride | 85.7 |
| | Octadecyltrimethylammonium chloride | 88.4 |
| | Tetra-n-butylammonium bromide | 81.8 |
| | Tetra-n-butylphosphonium bromide | 87.6 |
| | Cetyldimethylamine (Armean DM16D) | 59.0 |
| NONIONIC | Lissapol N (a nonylphenol ethoxylate) | 62.1 |
| | Pluronic L-64 (an ethylene oxide/propylene oxide block copolymer) | 65.9 |

EXAMPLE 30

2,2'-Azobis(2-methylpropanenitrile)

2,2'-Azobis(2-methyl-butanenitrile) and

2[(1-cyano-1-methylethyl)azo]-2-methylbutanenitrile 30 g of 2-amino-2-methylpropanenitrile (of 79.8% purity) was chlorinated by the method of Example 2. The pH was adjusted to 7 with caustic soda and 3 ml of "Arquad 16-29%" was added, followed by a further 2.2 equivalents of caustic soda. 22 g of 2-amino-2-methylbutanenitrile (of 94% purity) was then added slowly over one hour, the product was then stirred a further ten minutes and isolated by filtration. The yield of combined white solid azo compounds was 85% in a ratio of approximately 3:2:1 parts of 2,2'-Azobis(2-methylpropanenitrile), 2,2'-Azobis(2-methylbutanenitrile) and 2[(1-cyano-1-methylethyl)-azo]-2-methylbutanenitrile respectively.

EXAMPLE 31

2,2'-Azobis(2-methylbutanenitrile)

By the method of Example 2, 20 g of 94.2% pure 2-amino-2-methylbutanenitrile was chlorinated in water at 1060 mv and 20° C.

The resulting aqueous dispersion of N,N-dichloro-2-amino-2-methylbutanenitrile was adjusted to pH7 by the addition of caustic soda and 3 ml of "Arquad 16-29%" surfactant added. After addition of a further 2.2 equivalents of caustic soda, 16.8 gm of 2-amino-2-methylbutanenitrile were added slowly over 60 minutes whilst maintaining the temperature at 20° C. The resulting suspension was filtered, washed and dried to yield 28.6 gm of the title compound (yield 84.2%).

EXAMPLE 32

2,2'-Azobis(2-methylpropanenitrile)

30 gm of 2-amino-2-methylpropanenitrile (of 81.3% purity) was chlorinated by the method of Example 2 in water at 20° C. and 1060 mv.

The resulting aqueous dispersion of N,N'-dichloro-2-amino -2-methylpropanenitrile was adjusted to pH7 with caustic soda and 3 ml of "Arquad 16-29%" was added. A further 24.1 gm of 2-amino-2-methylpropanenitrile was then added, concurrently with sufficient caustic soda to maintain a pH of greater than 12, over 40 minutes and the resulting title compound was filtered off to yield 39.4 g (91.8% yield).

EXAMPLE 33

2,2'-Azobis(2-methylpropanenitrile)

By method of Example 2, 2-amino-2-methylpropanenitrile (of 78.5% purity) was dichlorinated and coupled with further 2-amino-2-methylpropanenitrile in the presence of caustic soda and the following combinations of tetra alkyl quaternary ammonium chloride surfactant and added sodium bromide. The yields of title compound obtained were as shown.

| Surfactant (mole %)* | Sodium Bromide mole %* | Yield % |
| --- | --- | --- |
| "Arquad 16-29%" (2%) | 0 | 90.4 |
| "Arquad 16-29%" (2%) | 0.2 | 92.9 |
| "Arquad 16-29%" (2%) | 0.4 | 93.7 |
| "Arquad 16-29%" (2%) | 2.0 | 93.1 |
| Cetyltrimethylammonium bromide (2%) | 0 | 94.2 |

*mole % based on 2-amino-2-methylpropanenitrile consumed.

EXAMPLE 34

2,2'-Azobis(2-methylpropanenitrile)

30 gm of 2-amino-2-methylpropanenitrile (of 80% purity) was added intermittantly to a stirred vessel containing 350 mls of water held at 20° C., and into which a constant stream of chlorine gas was passed such that the redox potential in the vessel was held at 1060 mv.

The resulting aqueous dispersion of N,N'-dichloro-2-amino-2-methylpropanenitrile was adjusted to pH7 with caustic soda and 3 ml of "Arquad 16-29%" was added.

A further 2.2 equivalents of caustic soda was added and the redox potential of the mixture fell to 500 mv.

2-amino-2-methylpropanenitrile was then added slowly at 20° C., until the redox potential fell to 400 mv. This required some 40 min and 26 gm of aminonitrile were added. The redox potential then rapidly fell to zero, and the slurry was filtered, washed and dried to yield 41 gm of the title compound (yield 93.8%).

EXAMPLE 35

2,2'-Azobis-(2,4-dimethyl-4-methoxy-pentanenitrile), and 2,2'-Azobis-(2-phenylpropanenitrile) may also be made by the above process.

We claim:

1. A process for the production of a compound of formula I,

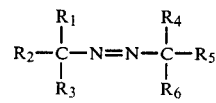

in which at least one of $R_1$, $R_2$ and $R_3$, and at least one of $R_4$, $R_5$ and $R_6$, represents an electron withdrawing group;

or one or both of $R_1$ and $R_2$, and $R_4$ and $R_5$, may together form a $-(CH_2)_n-$ chain, in which n is a whole number up to 5; the remainder of $R_1$, $R_2$, $R_3$, $R_4$, $R_5$ and $R_6$, which may be the same or different, each represent an electron withdrawing group, alkyl, cycloalkyl, phenyl or phenylalkyl;

the alkyl, cycloalkyl, phenyl or phenylalkyl group or the $-(CH_2)_n$ chain optionally being substituted by one or more hydroxy groups or acyl derivatives thereof, alkoxy groups, halogen atoms, or carboxylic acid groups or salts or esters thereof, in which at least one of $R_1$, $R_2$ and $R_3$, and at least one of $R_4$, $R_5$ and $R_6$ represents an electron withdrawing group, which comprises reacting one or more dichloramine compounds of formula II,

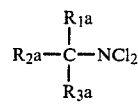

in which $R_{1a}$, $R_{2a}$ and $R_{3a}$ have the same significances as $R_1$, $R_2$, and $R_3$ above, with one or more compounds of formula III,

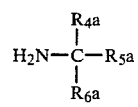

in which $R_{4a}$, $R_{5a}$ and $R_{6a}$ have the same significances as $R_4$, $R_5$ and $R_6$ above, the reaction being carried out in an aqueous medium in the presence of a base and a surfactant.

2. A process according to claim 1, wherein from 0.6 to 1.0 moles of the compound of formula III are reacted with each mole of the compound of formula II.

3. A process according to claim 1 or claim 2, wherein the reaction is carried out in the substantial absence of any solvent other than water.

4. A process according to claim 1, wherein the base is sodium hydroxide.

5. A process according to claim 1, wherein sufficient base is used to provide a pH of greater than 11 at the end of the reaction.

6. A process according to claim 1, wherein the reaction is carried out in the presence of bromide ions.

7. A process according to claim 1 wherein the reaction is monitored and controlled by means of its redox potential.

8. A process according to claim 1 which comprises reacting a compound of formula III with elemental chlorine and reacting the resulting dichloramine with a compound of formula III in an aqueous medium and in the presence of a base and a surfactant.

9. A process according to claim 1, wherein $R_3$ and $R_6$ are both —CN and $R_1$, $R_2$, $R_4$ and $R_5$ each contain up to and including 10 carbon atoms.

10. A process according to claim 1, wherein the compound of formula I is 2,2'-azobis-(2-methylpropanenitrile) or 2,2'-azobis(2-methyl-butane-nitrile).

* * * * *